(12) United States Patent
Deboer et al.

(10) Patent No.: US 6,309,371 B1
(45) Date of Patent: Oct. 30, 2001

(54) INJECTION-ASSISTING PROBE FOR MEDICAL INJECTOR ASSEMBLY

(75) Inventors: David M. Deboer, Brighton, MI (US); Peter L. Sadowski, Woodbury, MN (US); Paul R. Lesch, Jr., Lexington, MN (US); Claude L. Berman, St. Paul, MN (US); Lucio Giambattista, East Hanover, NJ (US)

(73) Assignees: Medi-Jet Corporation, Minneapolis, MN (US); Becton Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/359,790

(22) Filed: Jul. 26, 1999

Related U.S. Application Data

(60) Provisional application No. 60/094,167, filed on Jul. 27, 1998.

(51) Int. Cl.[7] .................................................... A61M 5/30
(52) U.S. Cl. ................................. 604/68; 604/69; 604/70
(58) Field of Search ............................... 604/68–72, 181, 604/187, 195, 196, 232, 239

(56) References Cited

U.S. PATENT DOCUMENTS

| | | |
|---|---|---|
| 2,322,244 | 6/1943 | Lockhart . |
| 2,380,534 | 7/1945 | Lockhart . |
| 2,398,544 | 4/1946 | Lockhart . |
| 2,547,099 | 4/1951 | Smoot . |
| 2,605,763 | 8/1952 | Smoot . |
| 2,650,591 | 9/1953 | Love . |
| 2,667,871 | 2/1954 | Hein, Jr. . |
| 2,667,874 | 2/1954 | Dickinson, Jr. . |
| 2,671,347 | 3/1954 | Scherer . |
| 2,675,802 | 4/1954 | Hein, Jr. . |
| 2,754,818 | 7/1956 | Scherer . |
| 2,762,369 | 9/1956 | Venditty . |

(List continued on next page.)

FOREIGN PATENT DOCUMENTS

| | | |
|---|---|---|
| 2071115 | 12/1992 | (CA) . |
| 959397 | 6/1964 | (GB) . |
| WO95/03844 | 2/1995 | (WO) . |
| WO96/19252 | 6/1996 | (WO) . |
| WO96/24398 | 8/1996 | (WO) . |
| WO96/28202 | 9/1996 | (WO) . |

*Primary Examiner*—Richard K. Seidel
*Assistant Examiner*—Lohn H. Thanh
(74) *Attorney, Agent, or Firm*—Pennie & Edmonds LLP

(57) ABSTRACT

A probe and nozzle assembly for reducing the pressure at which a needleless injector must deliver medicament for proper delivery are disclosed. In one embodiment of the probe, the probe is retractably located within an injector nozzle assembly. Upon activation of the energy source a portion of the probe extends past the nozzle assembly to deliver the medicament through a discharge channel. After activation the probe retracts back into the nozzle assembly. In another embodiment, the probe is fixed to the end of the nozzle assembly. In both embodiments the ratio of discharge channel length to diameter is greater than 6/1. The present invention also relates to nozzle assemblies with a discharge channel length to diameter ratio greater than 6/1.

9 Claims, 18 Drawing Sheets

U.S. PATENT DOCUMENTS

| | | |
|---|---|---|
| 2,896,977 | 7/1959 | Hansen . |
| 3,057,349 | 10/1962 | Ismach . |
| 3,066,670 | 12/1962 | Stauffer . |
| 3,138,157 | 6/1964 | Ziherl et al . |
| 3,292,622 | 12/1966 | Banker . |
| 3,330,276 | 7/1967 | Gordon . |
| 3,507,276 | 4/1970 | Burgess . |
| 3,515,130 | 6/1970 | Tsujino . |
| 3,688,765 | 9/1972 | Gasaway . |
| 4,089,334 | 5/1978 | Schwebel et al. . |
| 4,258,713 | 3/1981 | Wardlaw . |
| 4,266,541 | 5/1981 | Landau . |
| 4,296,747 | 10/1981 | Ogle . |
| 4,373,559 | 2/1983 | Mowles et al. . |
| 4,588,403 | 5/1986 | Weiss et al. . |
| 4,596,556 | 6/1986 | Morrow et al. . |
| 4,623,332 | 11/1986 | Lindmayer et al. . |
| 4,675,020 | 6/1987 | McPhee . |
| 4,719,825 | 1/1988 | LaHaye et al. . |
| 4,913,699 | 4/1990 | Parsons . |
| 4,940,460 | 7/1990 | Casey et al. . |
| 4,968,299 | 11/1990 | Ahlstand et al. . |
| 4,989,905 | 2/1991 | Rajecki . |
| 5,052,725 | 10/1991 | Meyer et al. . |
| 5,062,830 | 11/1991 | Dunlap . |
| 5,064,413 | 11/1991 | McKinnon et al. . |
| 5,112,317 | 5/1992 | Michel . |
| 5,114,406 | 5/1992 | Gabriel et al. . |
| 5,207,659 | 5/1993 | Pennaneac'h et al. . |
| 5,304,152 | 4/1994 | Sams . |
| 5,360,413 | 11/1994 | Leason et al. . |
| 5,383,851 | 1/1995 | McKinnon, Jr. et al. . |
| 5,399,163 | 3/1995 | Peterson et al. . |
| 5,454,805 | 10/1995 | Brony . |
| 5,476,449 | 12/1995 | Richmond . |
| 5,480,381 | 1/1996 | Weston . |
| 5,503,627 | 4/1996 | McKinnon et al. . |
| 5,531,255 | 7/1996 | Vacca . |
| 5,569,189 | 10/1996 | Parsons . |
| 5,593,390 | 1/1997 | Castellano et al. . |
| 5,599,302 | 2/1997 | Lilley et al. . |
| 5,704,911 | 1/1998 | Parsons . |
| 5,769,138 | 6/1998 | Sadowski et al. . |

INJECTION-ASSISTING PROBE FOR MEDICAL INJECTOR ASSEMBLY

This application is a continuation of provisional application No. 60/094,167 filed Jul. 27, 1998.

FIELD OF THE INVENTION

The present invention is directed to a device for delivery of medicament, and in particular to a jet injector with a skin tensioning probe to reduce the pressure at which the jet injector must eject the medicament for proper delivery.

BACKGROUND OF THE INVENTION

A wide variety of needleless injectors are known in the art. Examples of such injectors include those described in U.S. Pat. No. 5,599,302 issued to Lilley et al., U.S. Pat. No. 5,062,830 to Dunlap, and U.S. Pat. No. 4,790,824 to Morrow et al. In general, these and similar injectors administer medication as a fine, high velocity jet delivered under sufficient pressure to enable the jet to pass through the skin and enter the underlying tissues. These injectors typically have a nozzle assembly which has a barrel-like nozzle body having a medication holding chamber and an orifice through which a jet stream of medication is expelled from the chamber. Typically a plunger/piston actuated by an energy source, such as a coil spring, gas spring, or gas cartridge is used to expel the medicament.

Since at least the 1980s, the use of needleless injectors has become more desirable due to concerns over the spread of AIDS, hepatitis and other viral diseases caused by the possibility of accidental needle "sticks" from the conventional syringe and needle. One of the advantages associated with jet injectors is the absence of a hypodermic needle which removes apprehensions of healthcare workers and are superior in eliminating accidental disease transmission. Furthermore, given the aversion to needles possessed by some, the absence of a needle provides a psychological benefit. Even devices that utilize conventional hypodermic needles have attempted to capitalize on this psychological benefit. For example, self-injectors or auto-injectors like the ones disclosed in U.S. Pat. Nos. 4,553,962, 4,378,015 have retractable needles which are hidden until activation. Upon activation, the needle extends from the bottom of the device and penetrates the user's skin to deliver medicament. As none of these devices involves delivery of the medicament using jet injection, the medicament delivery location is limited by the length of the needle.

As the skin is a tissue composed of several layers and the injector is applied to the external surface of the outermost layer, the delivery pressure must be high enough to penetrate all layers of the skin. The layers of skin include, the epidermis, the outermost layer of skin, the dermis, and the subcutaneous region. The required delivery pressure is typically greater than approximately 4,000 p.s.i., as measured by the force of the stream of fluid divided by the cross-sectional area of the stream of fluid.

Although this pressure is readily achievable with most injectors, there are some circumstances in which delivery under a reduced pressure is desirable. For instance, certain medications which contain molecules with long protein chains can be sheared and rendered ineffective when expelled at high pressures. Reduced pressure delivery is particularly useful in intradermal applications such as vaccine, specifically DNA vaccines in which a high force energy mechanism could disrupt the molecular structure. See "Intradermal DNA Immunization by Using Jet-Injectors in Mice and Monkeys," *Vaccine*, 17:628–38, February 1999. Also, operation of the needleless injector at lower pressures can allow for a larger volume of medicament to be administered. Furthermore, the lower pressure could make manufacturing an injector device less expensive. The lower pressure would also reduce adverse stresses on the device and result in a corresponding increased useable device lifetime.

Thus, there exists a need for a jet injector with an injection assisting probe to reduce the pressure at which the jet injector must eject the medicament for proper delivery.

SUMMARY OF THE INVENTION

The present invention is drawn to a needleless injection system for injecting a medical product, and in particular, to a portable hand held device for injecting a medical product into a patient. The present invention is additionally drawn to an improved probe that can be used with a needleless injector.

The needleless injector according to the present invention comprises a nozzle assembly having an fluid chamber for holding the medical product and an energy mechanism or energy means. The nozzle assembly has an orifice in fluid communication with the fluid chamber for allowing passage of the medical product in and out of the fluid chamber. The nozzle assembly is preferably removably connected and can be prefilled with a medical product if desired or can even be of a disposable type. A probe extends from the nozzle assembly to tension the skin and allow the jet to puncture the taut skin at a pressure that is substantially lower than the pressure normally needed to penetrate the skin.

In one embodiment, the probe is retractably disposed within the nozzle assembly such that when the injector is fired, the probe is forced out of the end of the nozzle assembly. This stretches the skin, allowing the drug to enter the skin more easily. The diameter of the probe tip is smaller than the diameter of the opening at the distal end of the injector so that the probe tip can move within the opening. After the device has completed the injection, the probe is forced back into the nozzle assembly by a retractable means or mechanism. An O-ring or a spring typically provides the force necessary to retract the probe.

Another aspect of the present invention includes the use of different retracting means. Either a membrane, O-ring seal and spring, or a coil spring may be used in any combination for this purpose.

In another embodiment, the probe is rigidly disposed in the nozzle assembly in a fixed position and extends outwardly therefrom.

In another embodiment, the probe is a metal cylinder inserted or molded in the injector to provide a large discharge channel length to orifice diameter ratio, i.e., in the range of at least about 6/1 to as high as 20/1 or even greater.

In another embodiment, the rigid probe nozzle assembly is assembled from two separate pieces that can be joined either by being snapped together or otherwise interlocked, including by friction fitting, by being joined with an adhesive or by being ultrasonically bonded together.

In yet another embodiment, the nozzle ratio of discharge channel length to orifice diameter is large, i.e., in the range of at least about 6/1 to as high as 20/1 or even greater, with a long and gradual approach angle of about 3 to 30 degrees.

BRIEF DESCRIPTION OF THE DRAWINGS

These and other features, aspects, and advantages of the present invention will become much more apparent from the following description and accompanying drawings in which.

DESCRIPTION OF THE PREFERRED EMBODIMENTS

Figure 1:
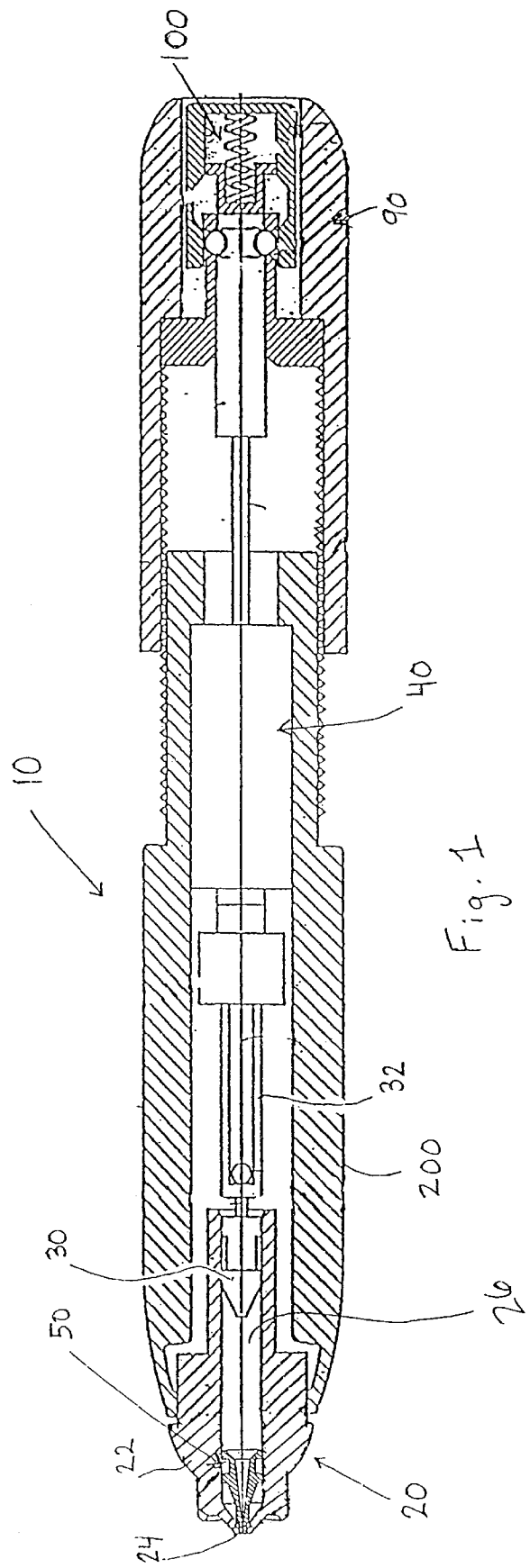
FIG. 1 is a cross-sectional view of a needleless injector with a nozzle assembly of a first embodiment of the injection assisting probe therein.

For convenience, the same or equivalent elements of the invention of embodiments illustrated in the drawings have been identified with the same reference numerals. Further, in the description that follows, any reference to either orientation or direction is intended primarily for the convenience of description and is not intended in any way to limit the scope of the present invention thereto.

As used in this application, the term distal shall designate the end or direction toward the front of the needileess injection device 10. The term proximal shall designate the end or direction toward the rear of the injector. The term longitudinal designates an axis connecting (the nozzle assembly 20 to the needleless injection device 10, and the term transverse designates a direction substantially perpendicular to the longitudinal direction including arcs along the surface of needleless injection device 10, or nozzle assembly 20.

Referring to FIG. 1, the needleless injection device 10 according to the present invention, comprises a nozzle assembly 20, an energy generating means 40 for forcing medicament out of the nozzle assembly, and an actuating mechanism 90, and a trigger assembly 100 for activating and triggering the energy mechanism 40. These components are operatively contained within a housing 200 as shown. It should be noted that energy generating means 40 can be a coil spring, gas spring, gas propellant, or any other force generating means.

The nozzle assembly 20 can be threadably connected to the housing 200 or the actuating mechanism 90 such that it can be readily attached and detached. In this manner, the needleless injection device 10 can be reused with various nozzle assemblies 20 that may contain different medications of different doses either together or at different times. For instance, the nozzle assembly 20 can be prefilled with medication and disposed of after each use. Further, a medication filling device such as a coupling device can be used to fill the fluid chamber with medication.

According to the first embodiment of the present invention, the nozzle assembly 20 has an injection assisting probe movable within a conventional nozzle body. The nozzle assembly 20 includes a nozzle member 22 having an opening 24 at the distal end, preferably having a diameter of about 0.04–0.4 inches, preferably of about 0.045 to 0.075 inches or any other suitable diameter that would allow for the introduction of an injection assisting probe therein. The nozzle member 22 includes a cylindrical fluid chamber 26 terminating at the distal end in a right circular cone 28. A plunger 30 having a pressure wall contoured to the cone 28 is positioned to slide within the fluid chamber 26. The plunger 30 can include sealing means such as one or more O-rings or the like (not shown) that are formed around its outer periphery to provide a seal, or the plunger itself can be a seal, as described in U.S. Pat. No. 5,062,830, the disclosure of which is incorporated herein by reference. The plunger can also include additional sealing means at spaced intervals to provide a better seal. In the embodiments shown, the plunger 30 is connected to a ram 32 which is connected to the energy mechanism 40. Alternatively the ram 32 can be integrally formed with an energy mechanism, if desired.

Figure 2:
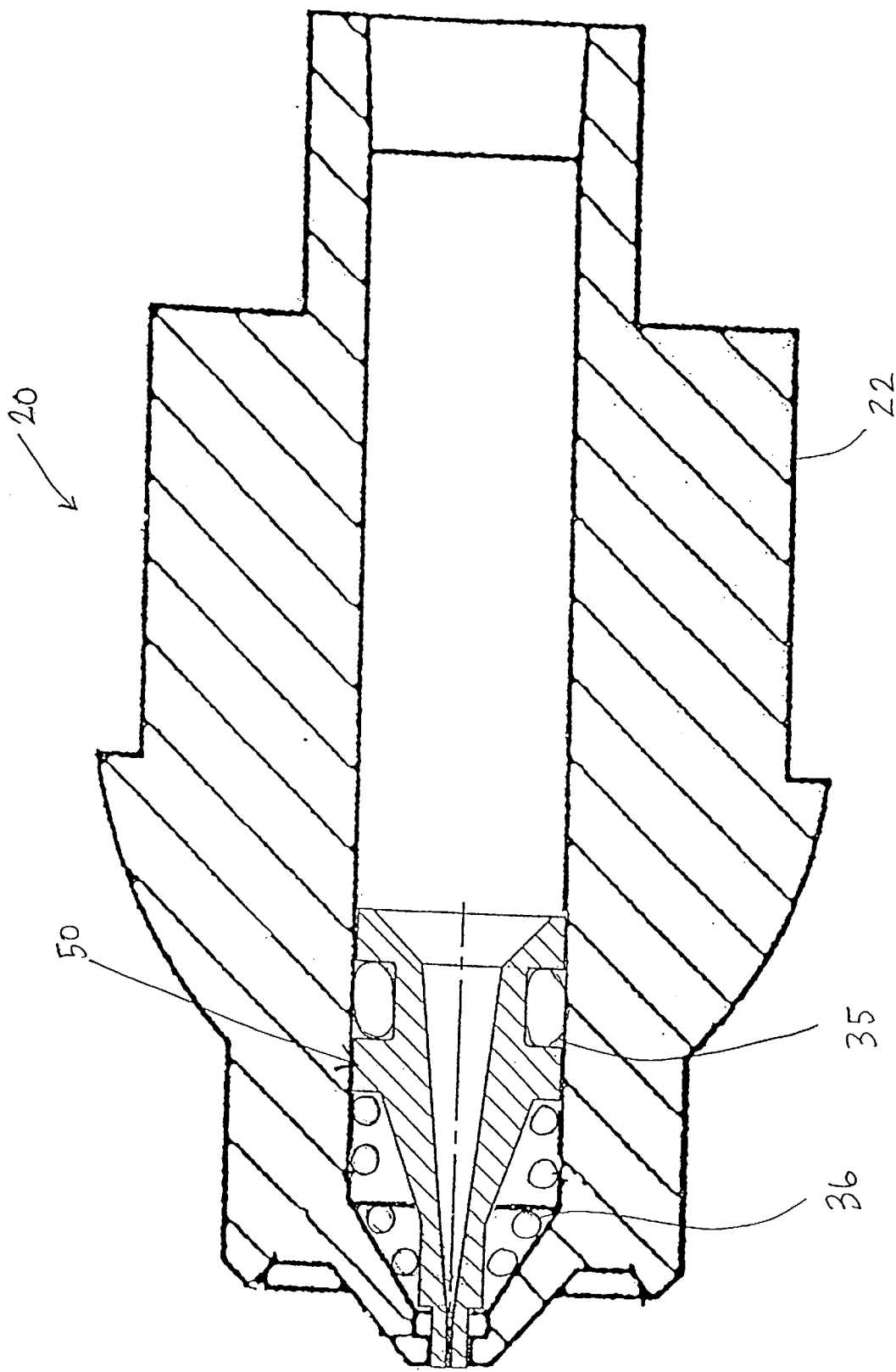
FIG. 2 is a cross-sectional view of the needleless injector nozzle assembly of FIG. 1 with the injection assisting probe in its neutral condition.
Figure 3:
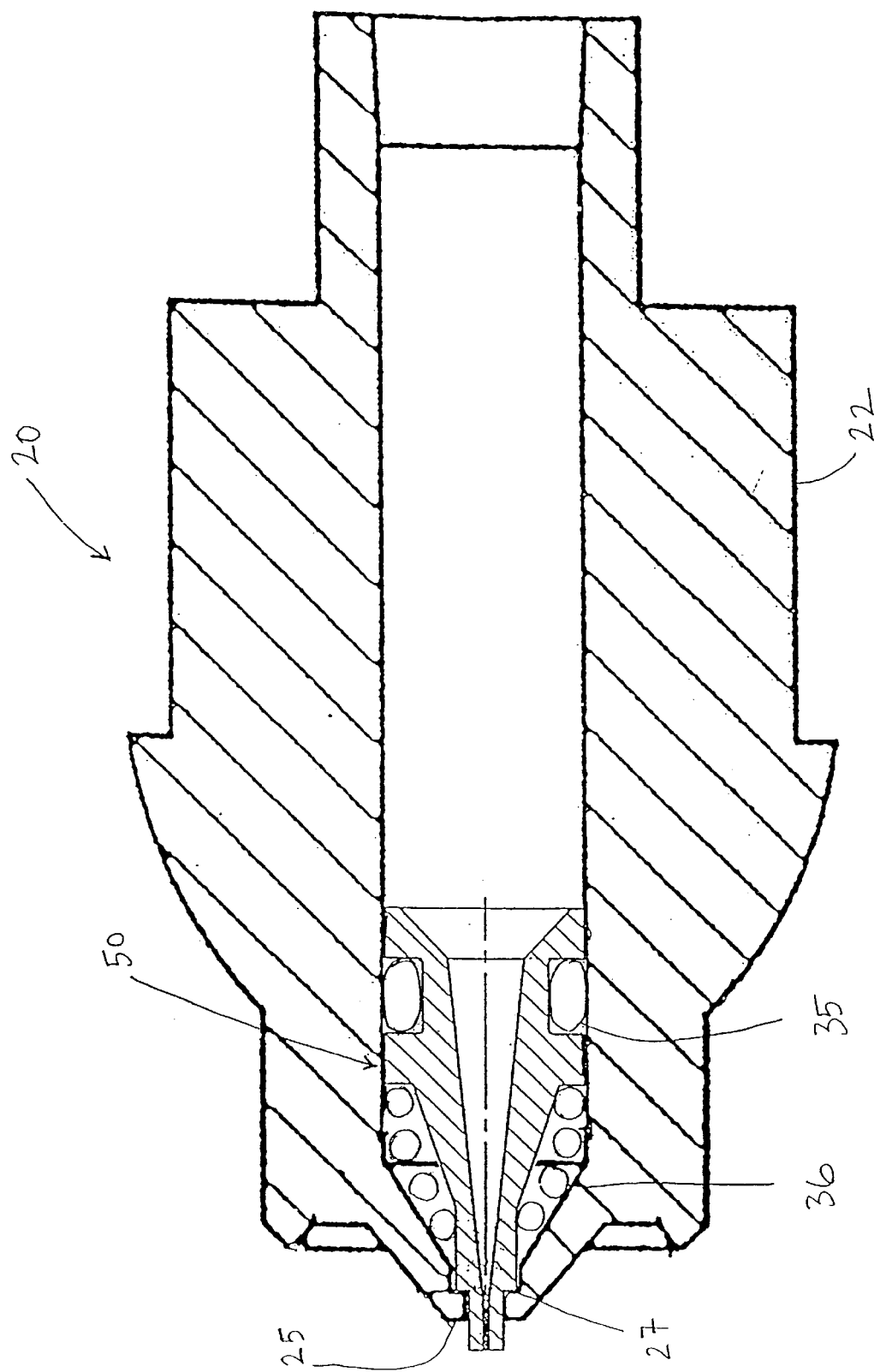
FIG. 3 is a view similar to FIG. 2, but with the injection assisting probe in its extended condition.
Figure 7:
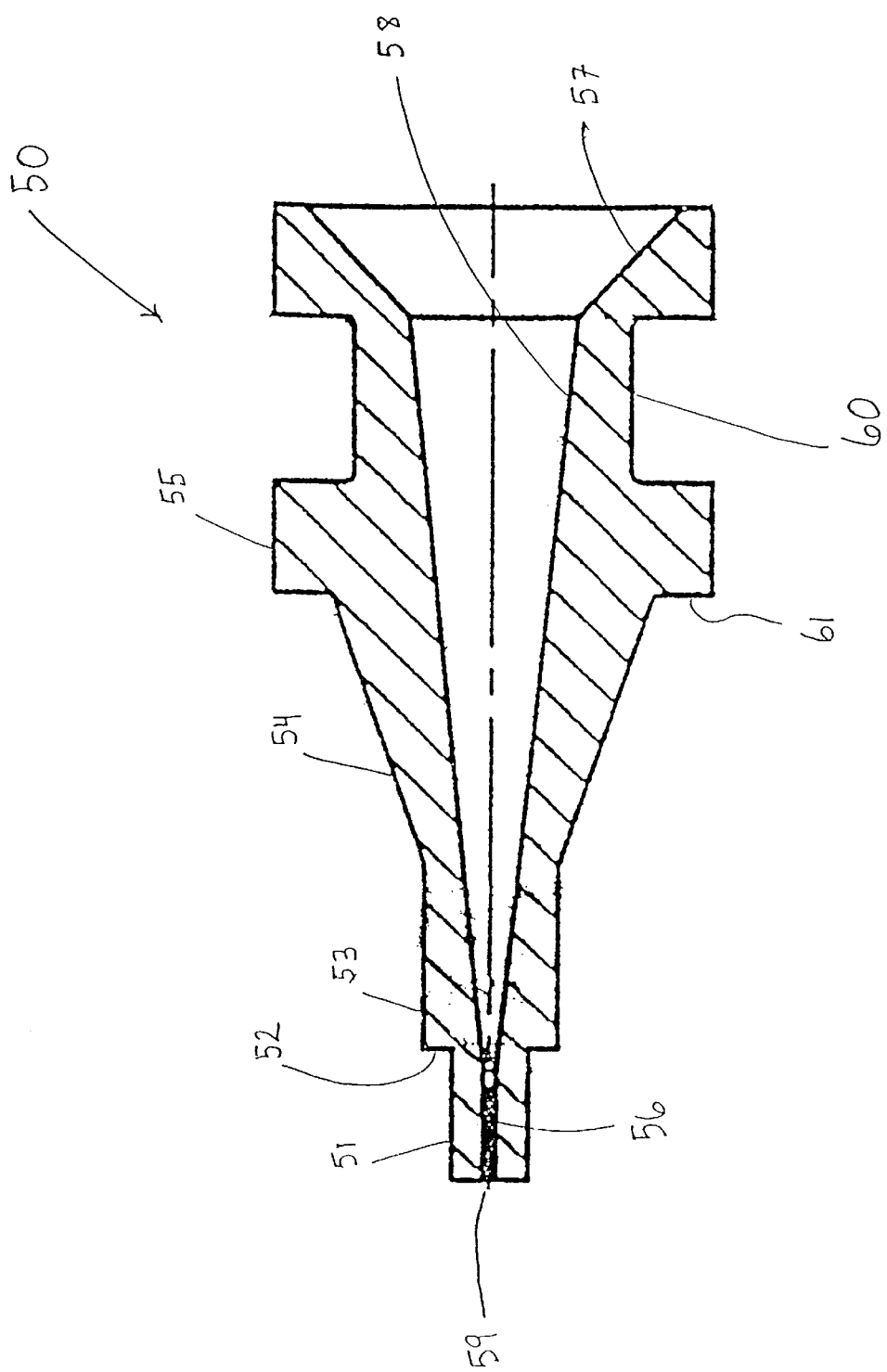
FIG. 7 is an enlarged cross-sectional view of the probe of the first embodiment.
Figure 8:
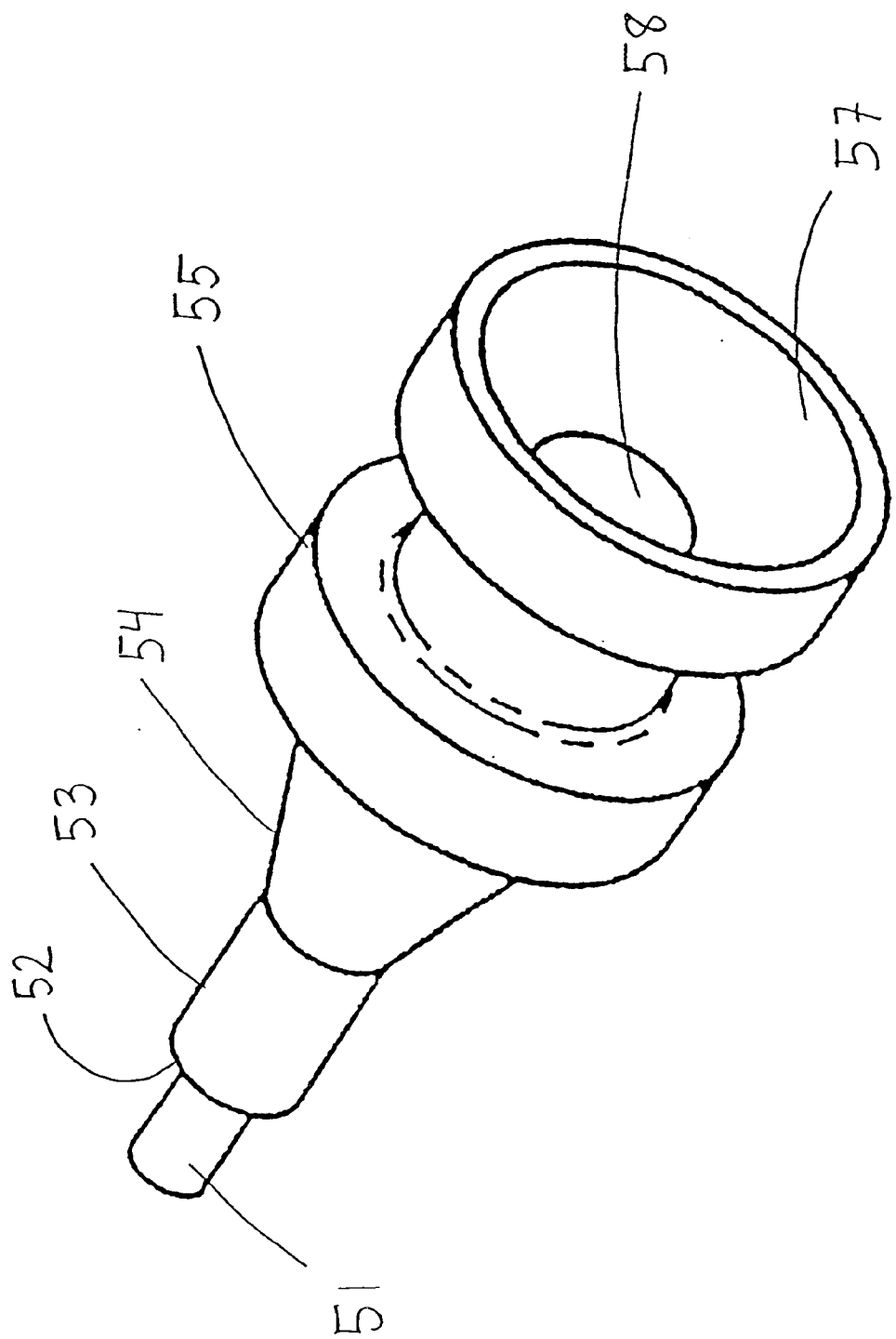
FIG. 8 is an enlarged perspective view of the probe of the first embodiment.

An injection assisting probe 50, as seen best in FIGS. 7–8, is positioned coaxially and retractably within the distal end of the fluid chamber 26. The injection assisting probe 50 has a plunger receptor 57 at the proximal end which is configured to accommodate the plunger 30 as it slides within the fluid chamber 26. Although the plunger receptor 57 can be of any shape conforming to the exterior profile of the plunger, it is preferably conical. The probe inner wall 58 is contoured to narrow like a funnel to the probe discharge channel 56. The probe discharge channel 56 extends to the discharge orifice 59 at the distal end of the probe. The probe discharge orifice 59 has a diameter of 0.004 to 0.012 inches. Preferably the diameter is 0.005 to 0.0075 inches. The discharge channel 56 is preferably cylindrical with a length to diameter ratio greater than 6. To provide a seal, the probe can include a sealing means such as an O-ring(s) 35 or the like, as shown in FIGS. 2 and 3, formed around its outer periphery and accommodated by slot 60 or the probe itself can be a seal. The probe preferably has a ridge 55, the distal surface of which provides an annular area that can compress a spring or other like retractable mechanism when the needleless injection device is triggered. Alternatively, a washer can be used instead of the ridge 55 to contain the O-ring 35 and compress the retracting mechanism during operation.

Figure 5:
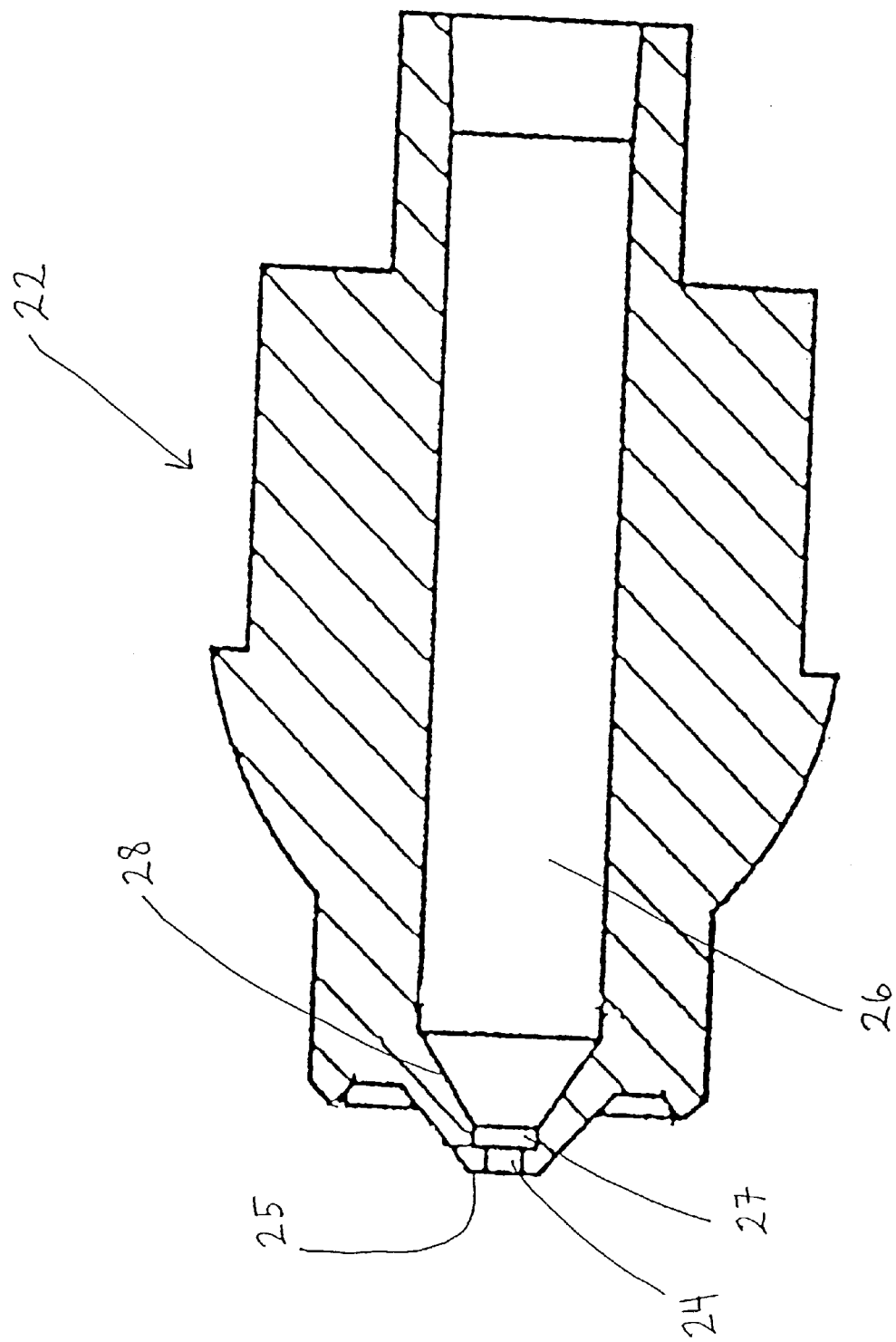
FIG. 5 is an enlarged cross-sectional view of a conventional nozzle body with a section bored out of the inner opening.
Figure 6:
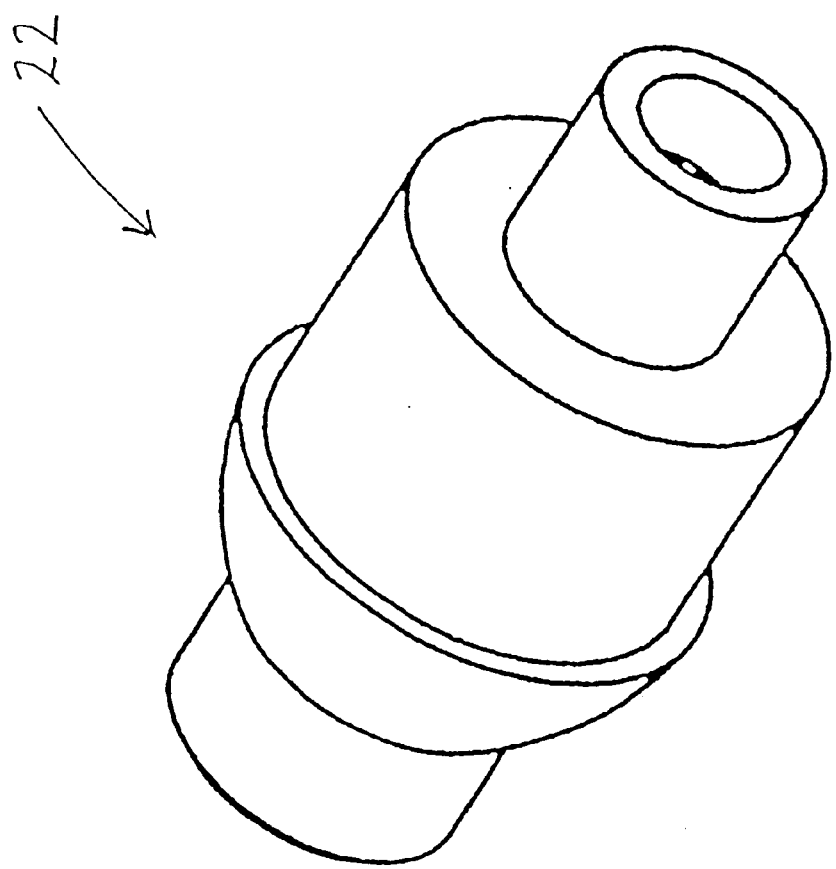
FIG. 6 is a perspective view of a conventional nozzle body.

FIGS. 5 and 6 show the nozzle assembly prior to introduction of the injection assisting probe. The outer periphery of the probe can be of varied geometries such that it fits within the nozzle member fluid chamber 26. Advantageously, the probe has a conical body section 54 which narrows gradually or tapers towards a cylindrical body section 53 of smaller circumference. Preferably, a shoulder 52 is positioned to separate the probe tip 51 from the cylindrical body section 53. The probe tip 51 is also cylindrical, but has a smaller circumference than the cylindrical body section 53 such that the probe tip can fit within and extend through the nozzle opening 24. The cylindrical body section 53 of the probe has a circumference such that the shoulder section 52, existing at the transition between the cylindrical body section 53 and the probe tip 51, prevents the cylindrical body section 53 of the probe from existing within the opening 24.

FIG. 2 illustrates the retractable injection assisting probe 50 in its neutral position while FIG. 3 illustrates the probe 50 in its extended position. In the extended position, the probe tip 51 extends beyond the distal end of the nozzle face 25. The shoulder 52 abuts the bored out inner section 27 of the nozzle opening to stop the probe from traveling further. The retracting mechanism, in this embodiment a spring, is compressed to provide a recoil force once the medicament is expelled.

Figure 4:
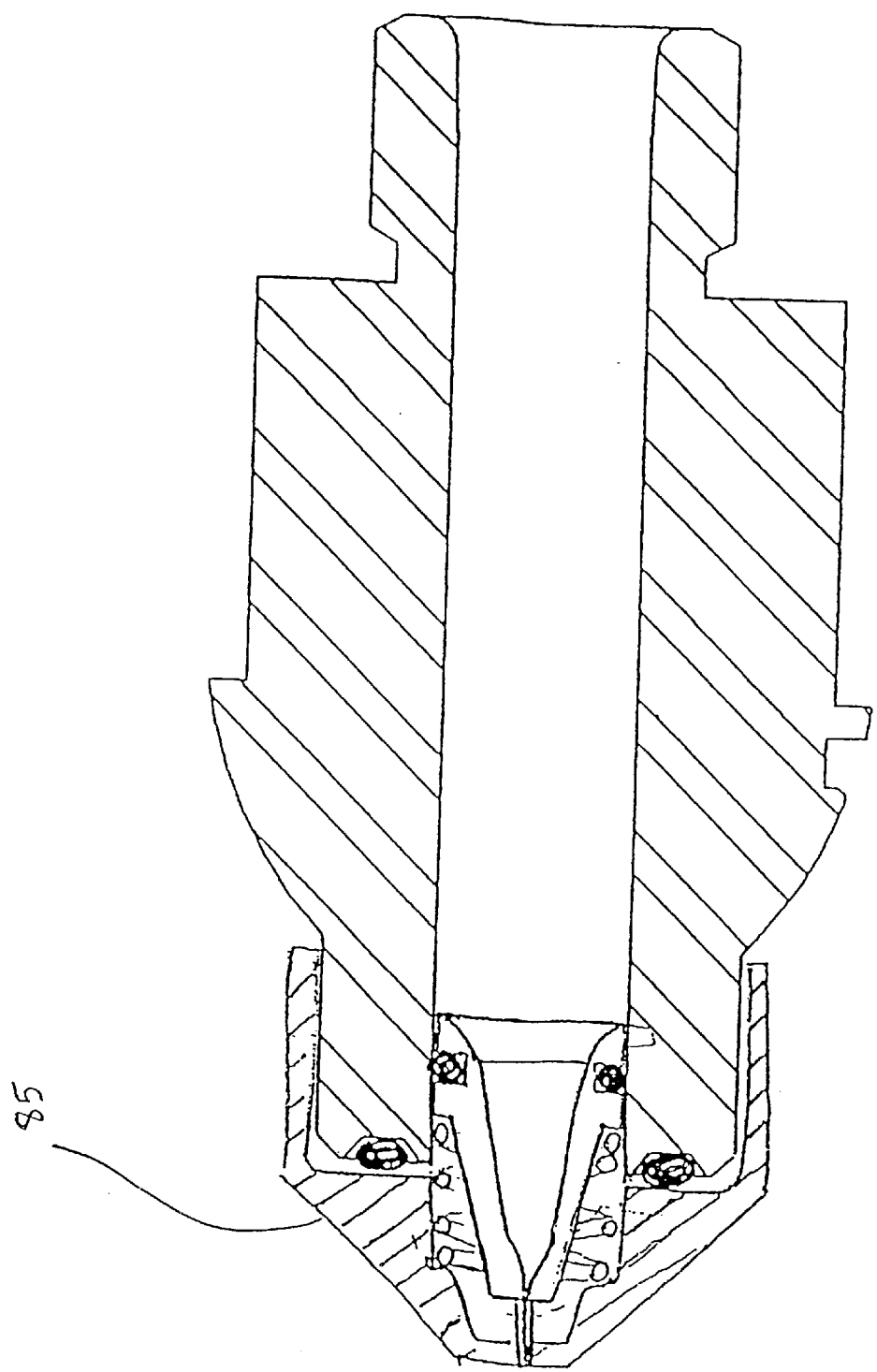
FIG. 4 is a cross-sectional view of another embodiment of a nozzle assembly according to the present invention.

FIG. 4 illustrates another aspect of the present invention where a nozzle assembly with a nozzle member cap 85 attached on, for example by screws, to a modified nozzle member wherein a retractable probe is disposed. Although FIG. 4 shows the retractable means as a spring, there is no limitation as to the retractable means which can be used with such a screw on nozzle assembly. In this regard, a resilient O-ring, a flexible membrane, a gas spring, or any other retractable means known to those skilled in the art can also be used.

Figure 9:
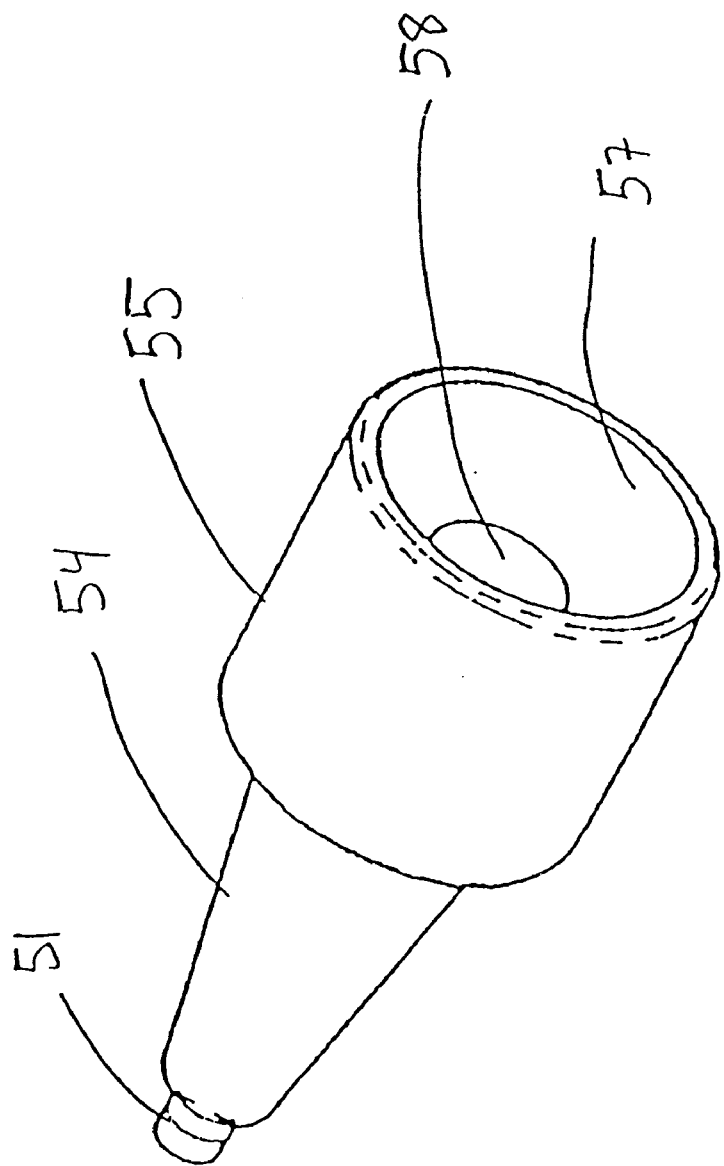
FIG. 9 is an enlarged perspective view of an alternate embodiment of the probe.
Figure 10:
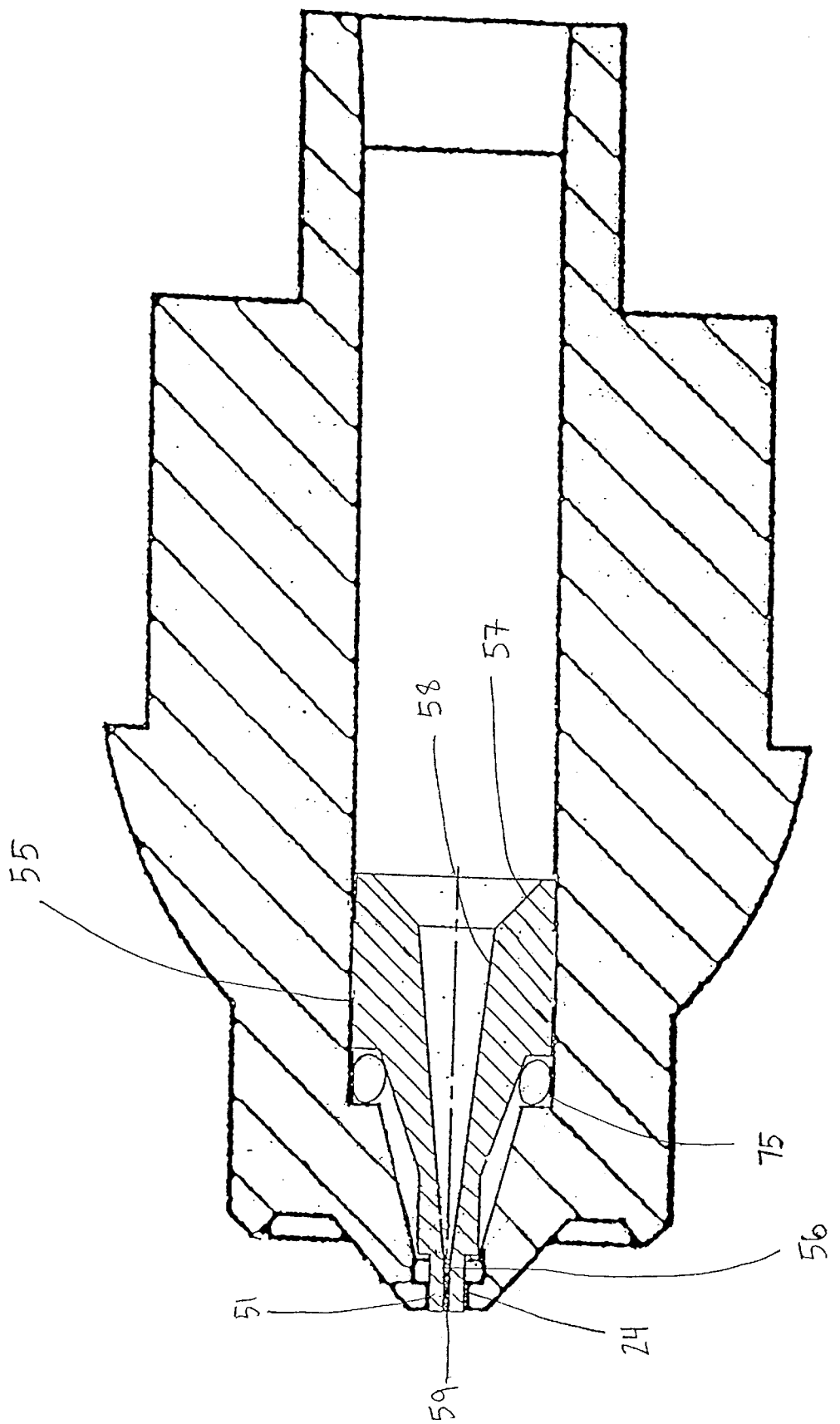
FIG. 10 is another embodiment of the nozzle assembly illustrated in FIG. 2, using a resilient O-ring as a retracting means and the probe of FIG. 9, showing the injection assisting probe in its neutral condition.
Figure 11:
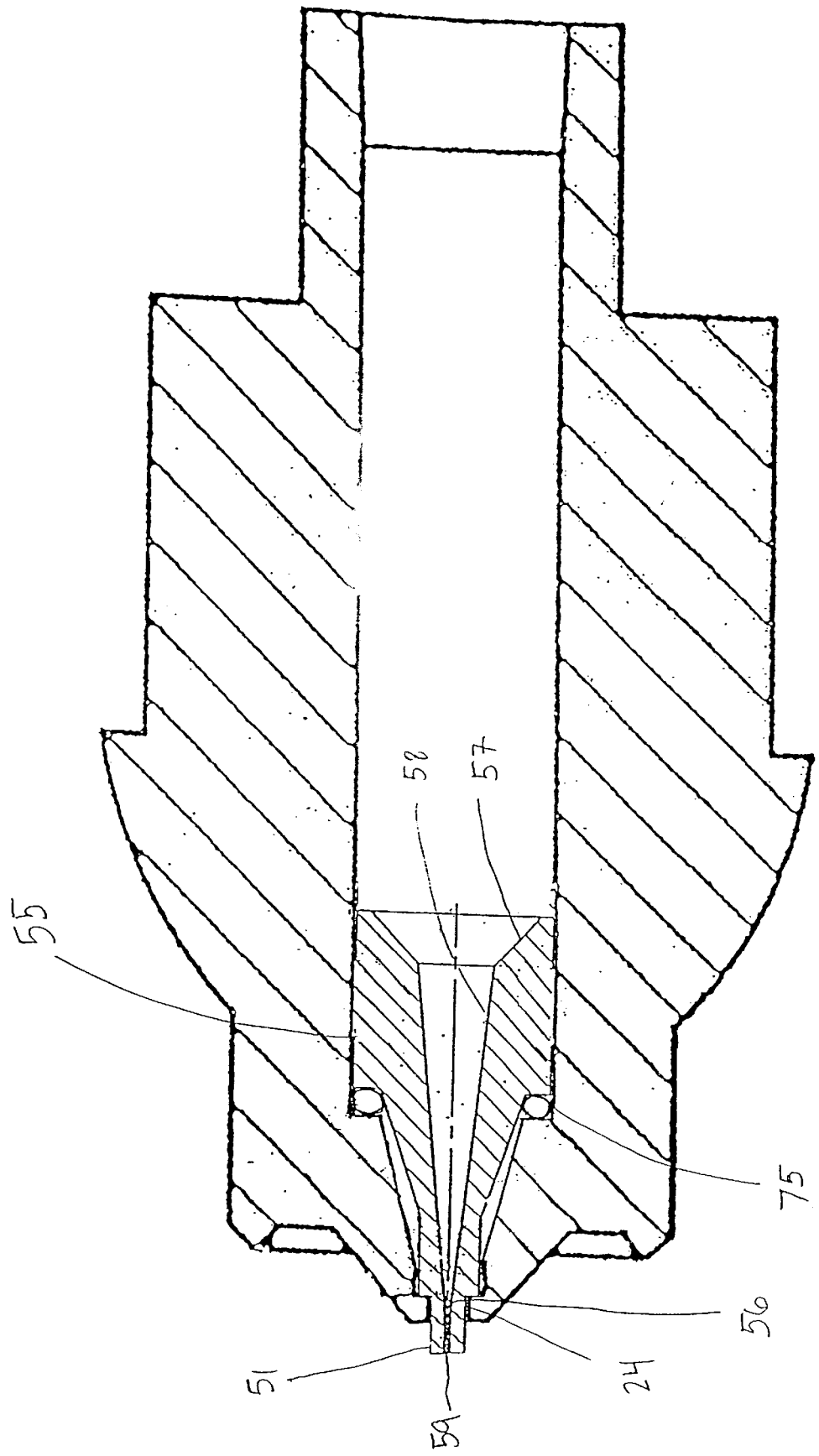
FIG. 11 is a view similar to FIG. 10, but with the injection assisting probe in its extended condition.

FIGS. 9, 10, and 11 show an alternative embodiment of the injection assisting probe in which the retraction mechanism is a resilient O-ring 75, or other like material known to those skilled in the art. A coil spring can be used instead of the O-ring. When the O-ring 75 is used, it can also act as a sealing mechanism, and for this reason the O-ring is preferred. The interior of the probe is similar to the other embodiments, with a section 57 to accommodate the plunger and a tapered section 58 to funnel the medicament to the discharge channel 56 and out the discharge orifice 59 during operation. FIG. 10 illustrates the neutral condition, before expelling medicament, and FIG. 11 shows the extended condition during which medicament is expelled. Similar to embodiments previously described, this embodiment functions to extend the probe tip 51 beyond the nozzle opening 24 and tension the patient's skin during operation. Also, similar to embodiments previously described, this retractable probe also preferably has a ridge 55 around the proximal end to provide a surface which compresses the resilient material when the injector is triggered.

Figure 12:
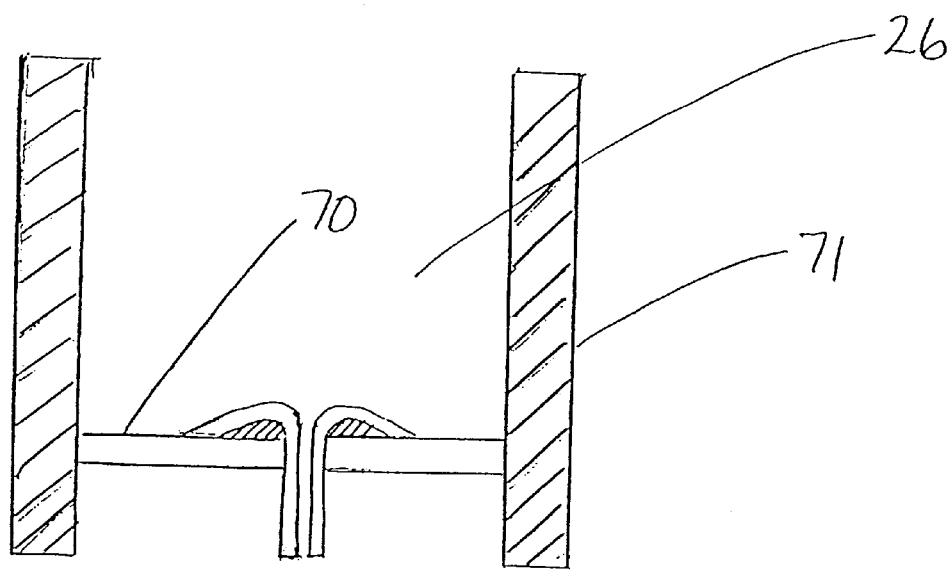
FIG. 12 is yet another embodiment of the nozzle assembly, using a flexible membrane as a retracting means, showing the injection assisting probe in its neutral condition.
Figure 13:
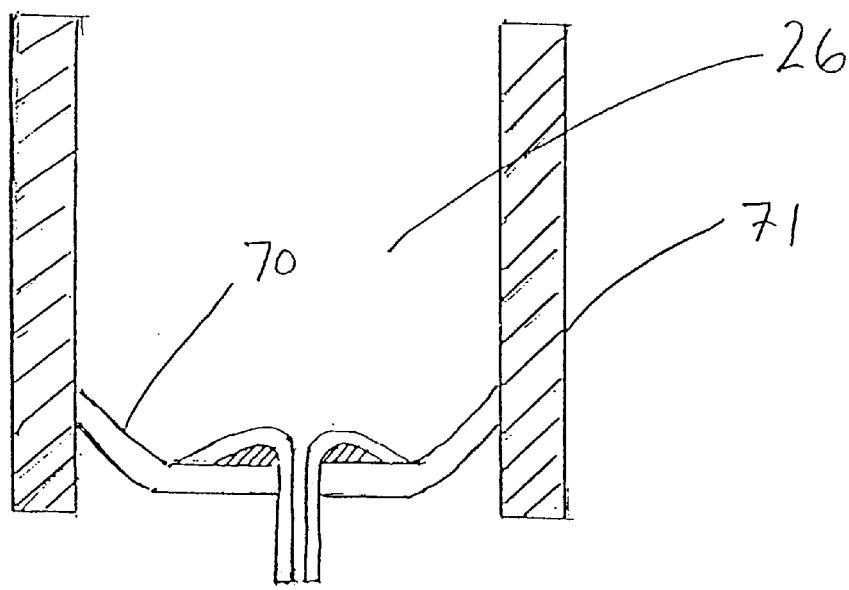
FIG. 13 is a view similar to FIG. 12, but with the injection assisting probe in its extended condition.

Another embodiment of the present invention, shown in FIGS. 12 and 13, is a variation of the retraction means wherein a flexible membrane is utilized. FIG. 12 illustrates the neutral condition before expelling the medicament. A flexible membrane 70 spans between nozzle walls 71 which define the sides of the fluid chamber 26 for holding medicament. Similar to embodiments previously described, the distal end of the nozzle walls act to guard the probe by extending beyond the membrane the same distance the probe does. The probe is attached to the flexible membrane by any conventional means known to those skilled in the art. Preferably, the probe is integrally attached to the flexible membrane with an adhesive. FIG. 13 shows the probe in its extended position where the probe extends beyond the end of the walls such that the probe tensions the skin to allow injection of the medicine at reduced pressure. Other embodiments of the present invention relate to a nozzle assembly with a fixed probe. Both a one-piece and a two-piece nozzle assembly with a fixed probe can be used and are contemplated by this invention.

Figure 14:
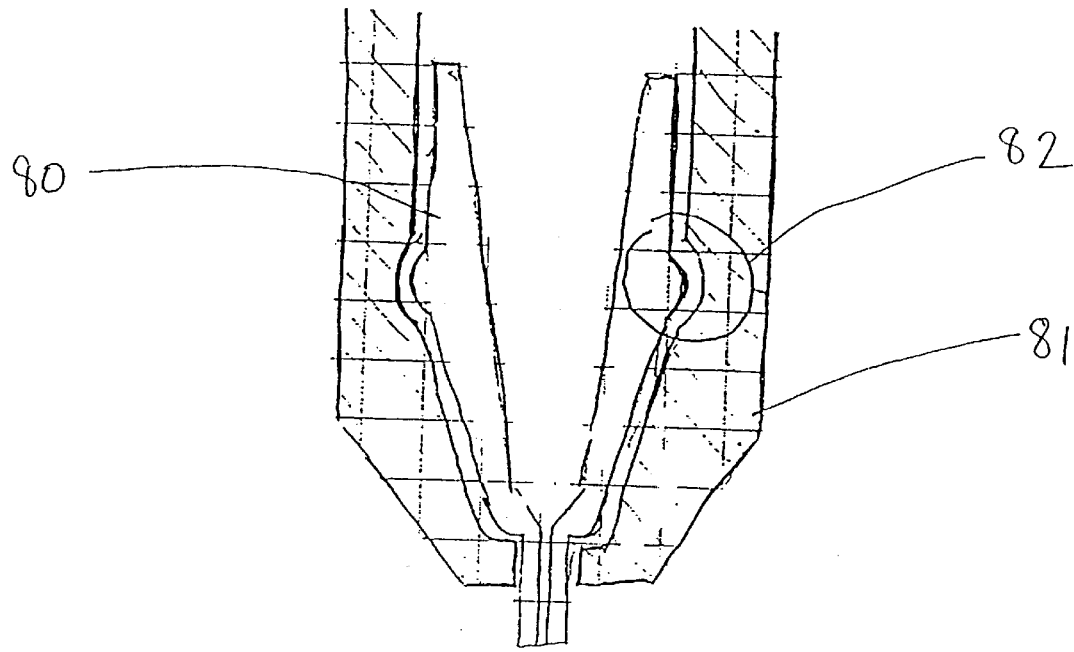
FIGS. 14 and 15 illustrate a two-part nozzle assembly with a fixed probe wherein the probe member and nozzle member snap together.
Figure 15:
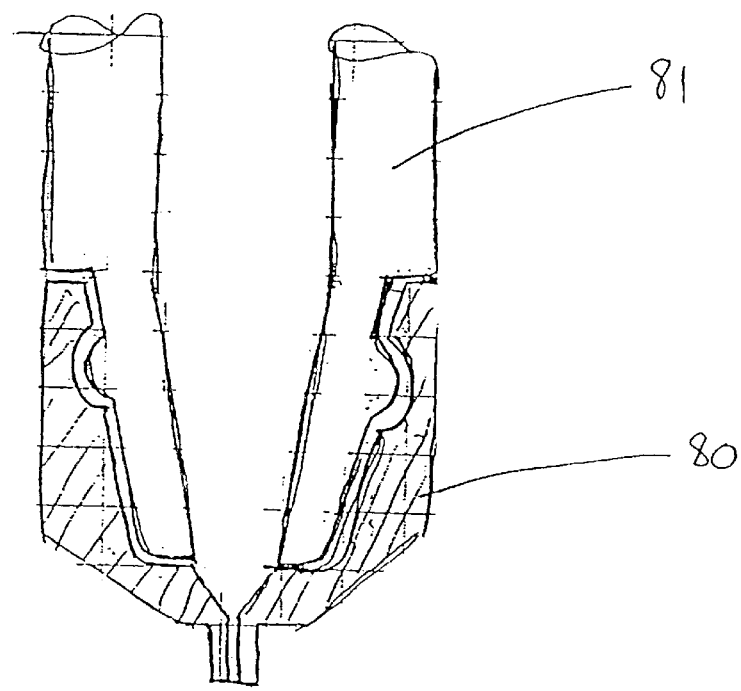
Figure 16:
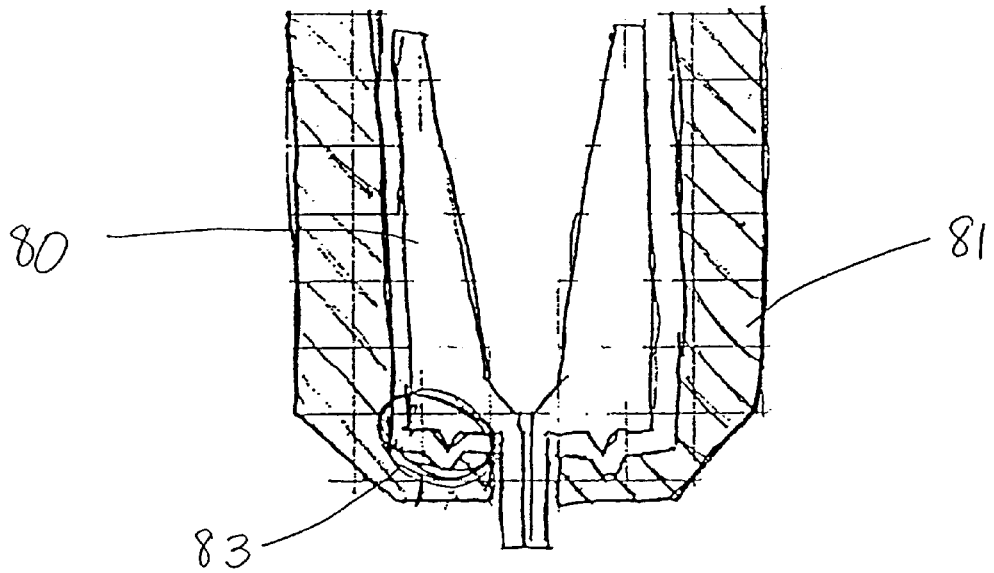
FIG. 16 illustrates a two-part nozzle assembly with a fixed probe wherein the probe member and nozzle member are ultrasonically welded together.
Figure 17:
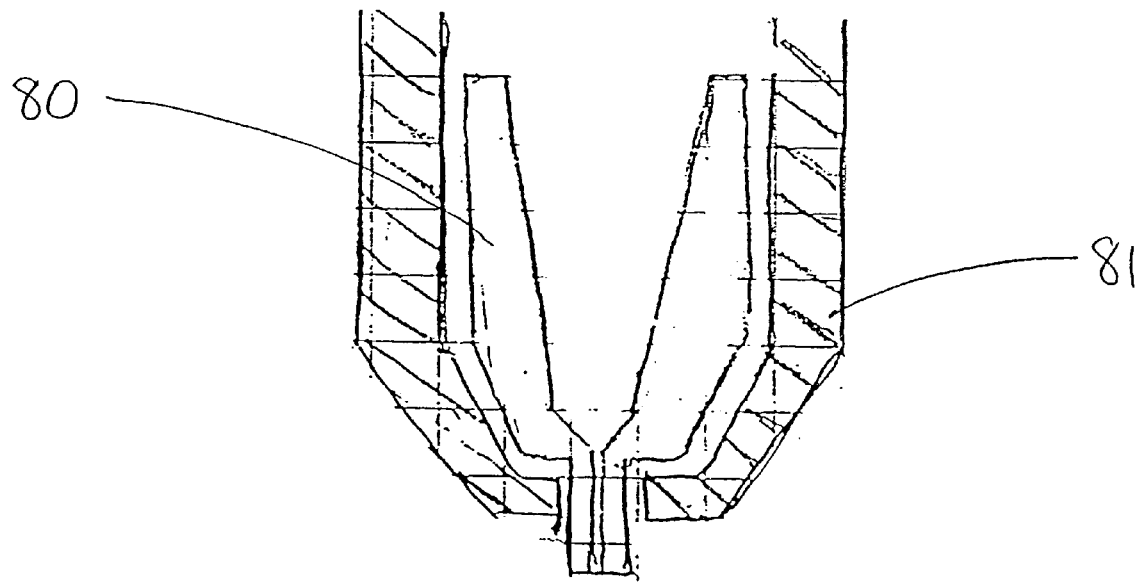
FIG. 17 is a view similar to FIG. 16, but uses a solvent or adhesive bonding means.

FIGS. 14–17 show embodiments of the present invention with a two piece nozzle assembly with a fixed probe. The probe bearing section 80 can either be attached internally or externally from the nozzle member. Although, any conventional attaching means can be used, FIGS. 14 and 15 show a preferable friction-fitting or snapping attaching means for both internal and external attachment of the probe bearing member respectively. FIG. 16 shows a preferable ultrasonic bonding means of attachment for the probe. Although, the ultrasonic bonding features 83 can be placed at any location to attach the two pieces, preferably, the ultrasonic bonding features 83 are along the distal end at the interface between the probe member 80 and the nozzle member 81 to facilitate ease of manufacturing. FIG. 17 shows a preferable solvent bonding or adhesive bonding means of attachment.

Figure 19:
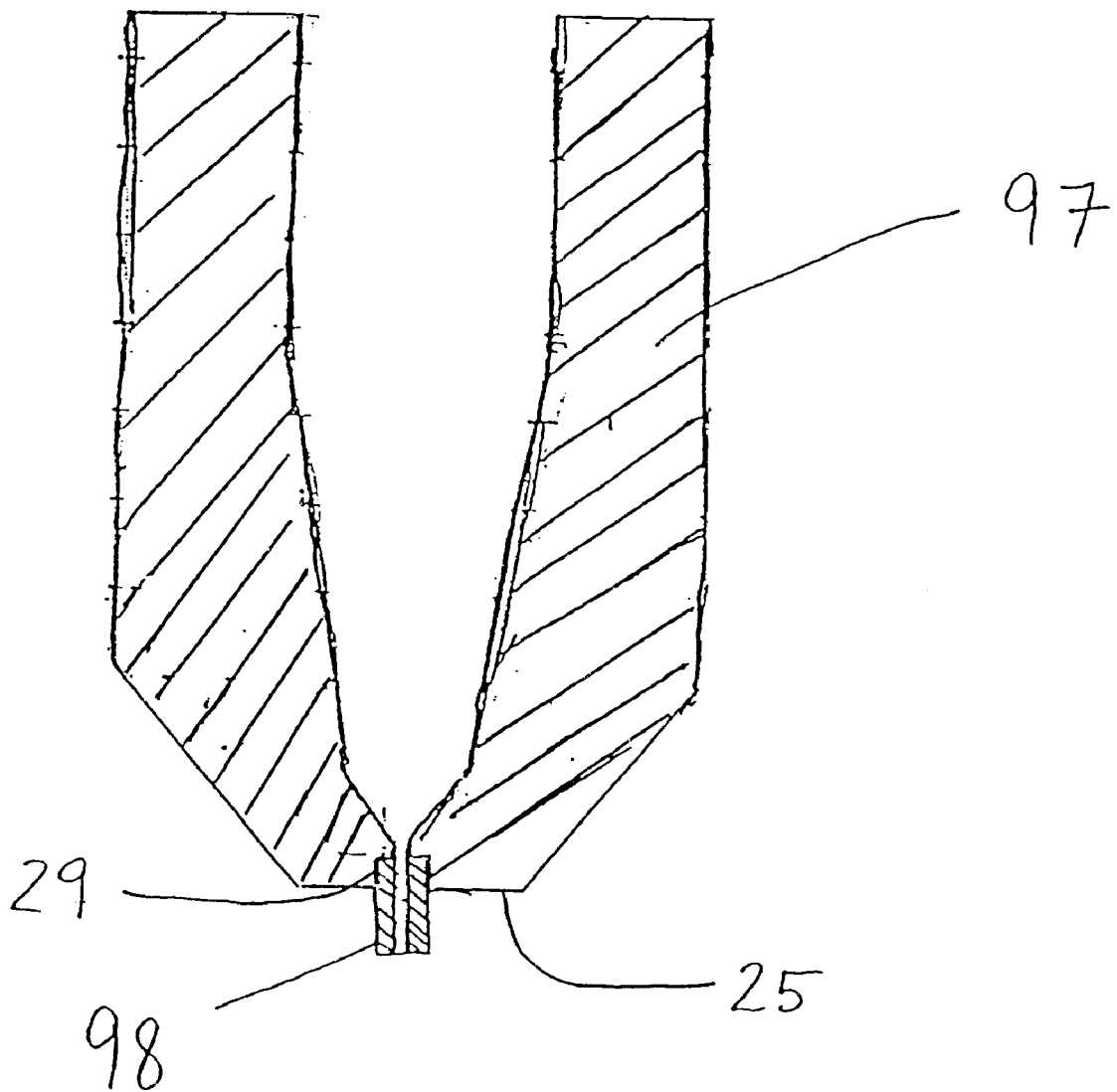
FIG. 19 is a view of another embodiment of a multi-piece nozzle assembly with a fixed probe formed by a tubular insert.

Another embodiment of a multi-piece nozzle assembly with a fixed probe is shown in FIG. 19. The nozzle assembly consists of a nozzle member 97 similar to a conventional nozzle member with the exception that the nozzle face 25 has a bore 29 coaxial with the center of the nozzle member 97 which is designed to receive a tubular insert 98 to create a fixed probe. Although the tubular insert 98 can be made of any suitable material, preferably the insert is stainless steel. The interior of the tubular insert 98 is cylindrical and functions as the discharge channel once it is inserted into the nozzle. Similar to previously described embodiments, the ratio of discharge channel length to orifice diameter is greater than 6. Also similar to other embodiments of the present invention, once inserted into the nozzle member, the tubular insert extends beyond the distal face of the nozzle. Preferably the tubular insert extends by 0.04 to 0.08 inches beyond the nozzle face.

Figure 20:
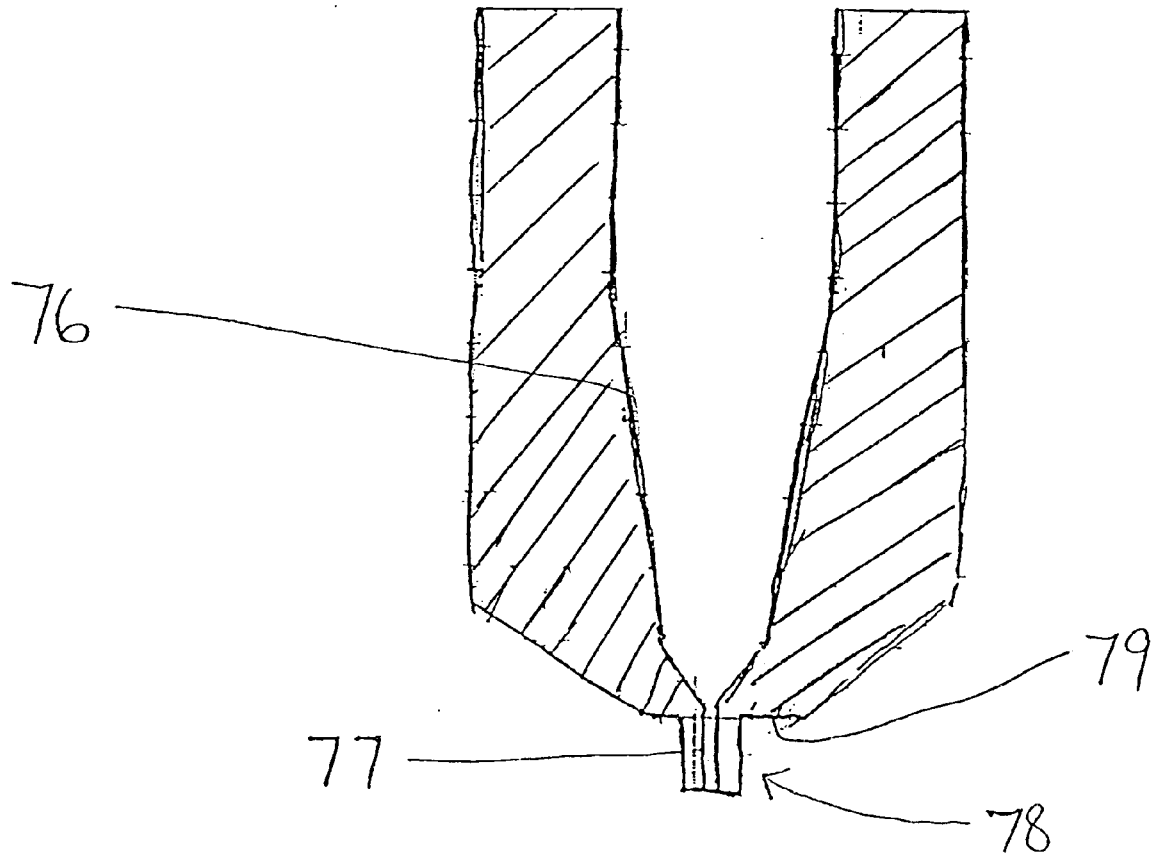
FIG. 20 illustrates another embodiment of a fixed probe which has a one-piece nozzle assembly.

FIG. 20 illustrates another embodiment of a fixed probe which has a one-piece nozzle assembly. Similar to embodiments described previously, the nozzle assembly has a funnel-like conical section 76 which tapers toward the discharge channel 77 at the distal end. The nozzle member of this embodiment is similar to the conventional nozzle member, with the exception that a probe 78 is integral with and extends outwardly from the nozzle distal face 79.

Figure 21:
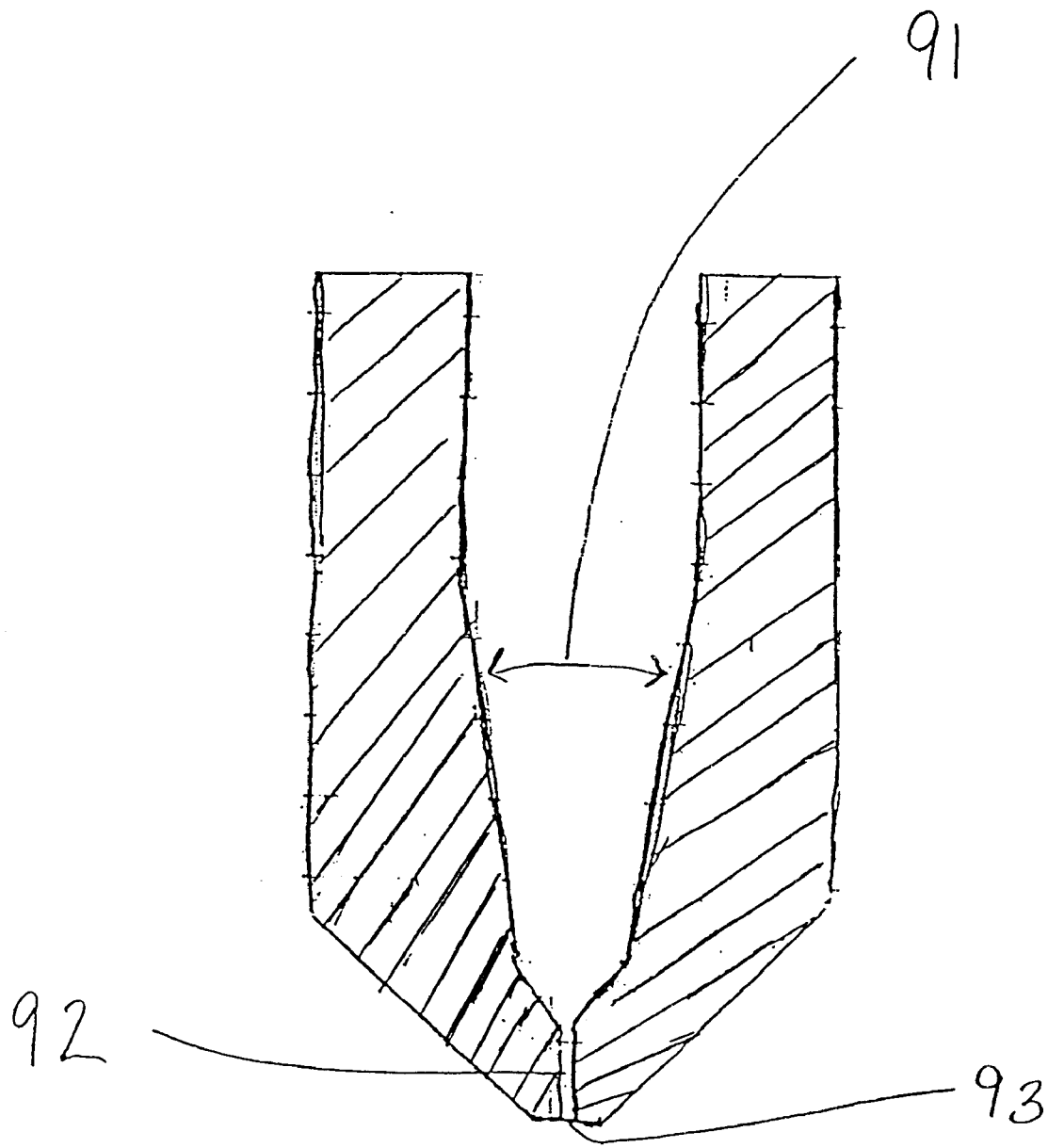
FIG. 21 illustrates yet another embodiment where the nozzle ratio of discharge channel length to orifice diameter is large with a long and gradual approach angle.

FIG. 21 shows an alternative embodiment of the present invention which relates to nozzles having large length to diameter ratios, either with or without a probe attached at an end of the nozzle. In FIG. 21 and throughout this application, diameter refers to the diameter of the discharge orifice 93 and length refers to the length of the discharge channel 92 or cylindrical section of the nozzle leading to the orifice. Currently, commercially available injectors have a length to diameter ratio of approximately 4/1 to 6/1. The length to diameter ratio of a nozzle according to the present invention is greater than 6/1. Preferably the ratio is at least 9/1 or even greater. As pressure is determined by force divided by cross-sectional area, using a nozzle assembly with a large length to diameter ratio allows the use of a lower force energy mechanism without a reduction of pressure. Preferably, such a nozzle also has a long and gradual approach angle 91 leading to the discharge channel 92 of about 3 to 30 degrees.

Figure 18:
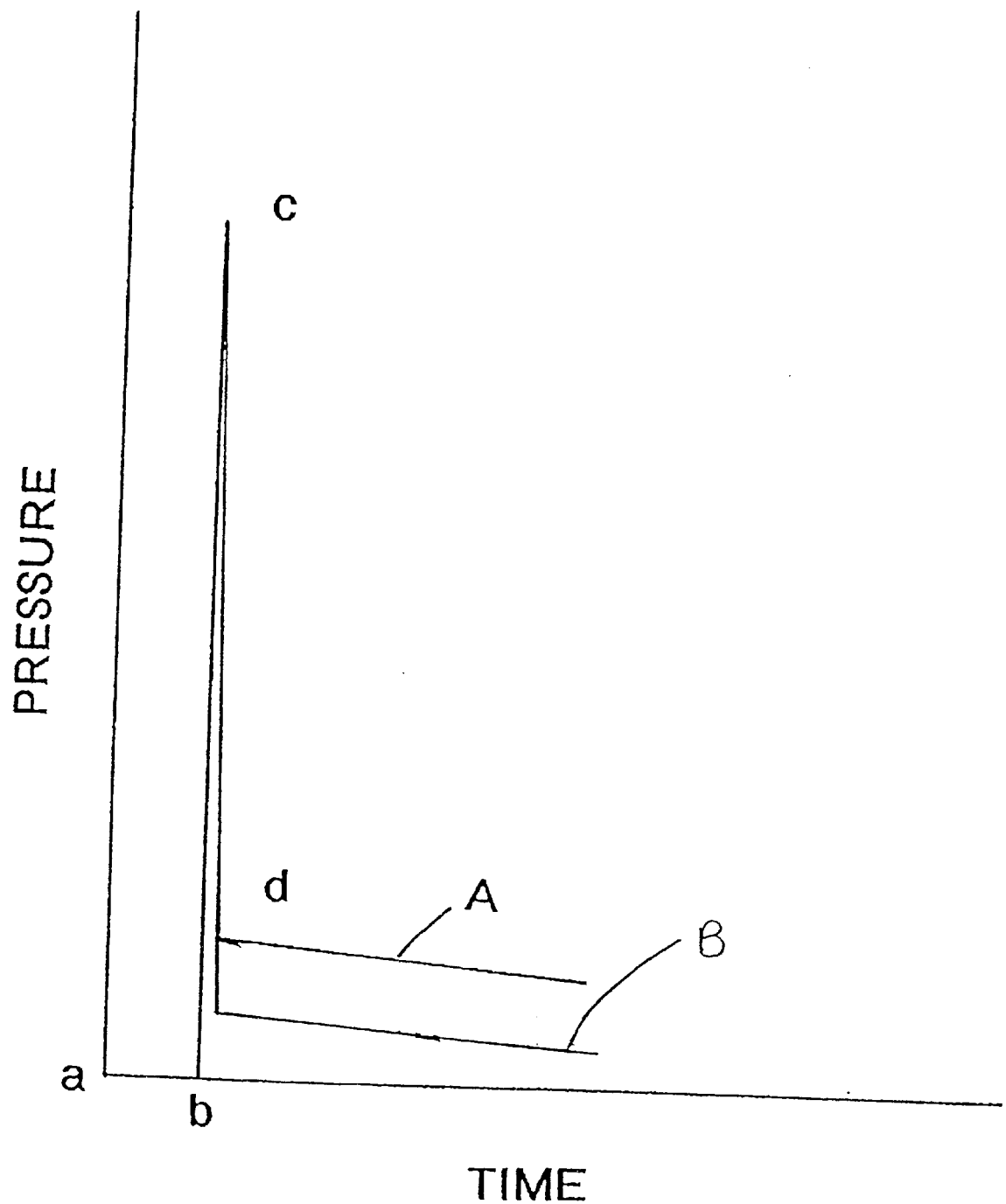
FIG. 18 shows an exemplary sample of a graph expressing a pressure-time curve between a conventional needleless injection device and an injection assisting probe device according to the present invention.

A significant advantage of the injection-assisting probe is that it allows for a lower pressure to break the skin barrier and administer the medicament. In this regard, administering an injection using either a fixed or retractable probe requires less energy and force than conventional needless injector devices. FIG. 18 shows a pressure-time curve for a conventional injector, Curve A, which delivers a jet stream at steady state pressures around 4,000 psi., as measured by the force of the stream of fluid divided by the cross-sectional area of the stream of fluid. Needleless injectors utilizing, an injection-assisted probe, however, need only to achieve a lower steady state pressure as shown by curve B while maintaining the quality of the injection. Specifically, experimentation has shown that the same percentage of successful injections can be achieved with needleless injectors having a probe of the present invention and 40 lb. energy generating means as with conventional needleless injectors having 55 lb. energy generating means. Furthermore, when injectors with the same energy generating means are compared with and without a probe of the present invention, the percentage of successful injections is increased with a probe. For instance, for an injector with a retracting probe, 100% of the injections in experimentation were successful, while only 68% of injections were successful without a probe. Injectors with a fixed probe were also advantageous, yielding 98% successful injections.

Fabricating a nozzle assembly of two parts as described above facilitates manufacturing of a nozzle assembly with a large length to diameter ratio. Furthermore, the discharge channel 92 or cylindrical section leading to the discharge orifice 93 can be a metallic tube having the desired length to diameter ratio. As it is particularly problematic to fabricate nozzle assemblies with large length to diameter ratios out of plastic components, use of a metallic tube in conjunction with a plastic nozzle assembly is preferred.

While it is apparent that the illustrative embodiments of the invention herein disclosed fulfill the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. An injection device comprising:
   a housing;
   an injection-assisting probe retractably located at a distal end of an injection device;
   a nozzle assembly having an opening for slidingly receiving at least a portion of the probe and defining a fluid chamber and being removably associated with the housing;
   a trigger assembly;
   a plunger; and
   an energy generating source operatively associated with the trigger assembly so that movement of the trigger assembly activates the energy source to move the plunger in a first direction and expel a fluid from the fluid chamber;
   wherein said injection-assisting probe comprises:
      a probe tip located at a distal end of the probe with at least a portion configured and dimensioned to slide within and to extend beyond the nozzle assembly opening the nozzle assembly opening;
      a discharge channel within the probe tip and terminating in an orifice through which the fluid is expelled;
      a body portion extending towards the discharge channel;
      a plunger receptor configured and dimensioned to receive at least a portion of the plunger; and
      a retraction element operatively associated with the nozzle assembly, wherein
         the probe is located within the nozzle assembly in a retracted position prior to activation of the energy source;
         movement of the plunger in the first direction upon activation of the energy source results in at least a portion of the probe tip extending from the nozzle assembly opening such that the probe tip protrudes beyond the nozzle assembly opening; and
         the retraction element returns the probe tip to the retracted position after activation of the energy source.

2. The injection device of claim 1, wherein the retraction element is one of a resilient O-ring, a spring, or a flexible membrane.

3. The injection device of claim 1, wherein the body portion has an exterior surface that includes a ridge for accommodating the retraction element.

4. The injection device of claim 1, wherein a shoulder is disposed between the probe tip and the probe body for limiting the portion of the probe tip that extends from the nozzle assembly opening.

5. The injection device of claim 1, wherein the discharge channel has a length and a ratio of the discharge channel length to orifice diameter is greater than 6.

6. The injection device of claim 1, wherein the orifice diameter is between 0.004 to 0.012 inches.

7. The injection device of claim 1, wherein the discharge channel has a length of at least 0.024 inches.

8. The injection device of claim 1, wherein the body portion has a funnel-shaped interior which tapers toward the discharge channel.

9. The injection device of claim 1, wherein the nozzle assembly comprises two sections.

* * * * *

UNITED STATES PATENT AND TRADEMARK OFFICE
CERTIFICATE OF CORRECTION

PATENT NO. : 6,309,371 B1
DATED : October 30, 2001
INVENTOR(S) : Deboer et al.

It is certified that error appears in the above-identified patent and that said Letters Patent is hereby corrected as shown below:

<u>Title page,</u>
At "[73] Assignees": change "Medi-Jet Corporation" to -- Medi-Ject Corporation --.

<u>Column 8,</u>
Line 12, delete " the nozzle assembly opening"

Signed and Sealed this

Twenty-third Day of April, 2002

Attest:

Attesting Officer

JAMES E. ROGAN
*Director of the United States Patent and Trademark Office*